United States Patent
Williams (10) Patent No.: US 10,798,921 B2
(45) Date of Patent: Oct. 13, 2020

(54) METHOD FOR REDUCING PATHOGENS IN POULTRY HATCHERY OPERATIONS

(71) Applicant: Zoetis Services LLC, Parsippany, NJ (US)

(72) Inventor: Christopher John Williams, Apex, NC (US)

(73) Assignee: Zoetis Services LLC, Parsippany, NJ (US)

( * ) Notice: Subject to any disclaimer, the term of this patent is extended or adjusted under 35 U.S.C. 154(b) by 337 days.

(21) Appl. No.: 15/884,467

(22) Filed: Jan. 31, 2018

(65) Prior Publication Data

US 2018/0220626 A1    Aug. 9, 2018

Related U.S. Application Data (60) Provisional application No. 62/455,761, filed on Feb. 7, 2017.

(51) Int. Cl.
*A01K 43/00* (2006.01)
*G01N 33/08* (2006.01)
(Continued)

(52) U.S. Cl.
CPC ............ *A01K 43/00* (2013.01); *A01K 45/007* (2013.01); *G01N 33/08* (2013.01); *G01N 33/085* (2013.01); *A01K 41/06* (2013.01)

(58) Field of Classification Search
CPC ....... A01K 43/00; A01K 45/007; G01N 33/08
(Continued)

(56) References Cited

U.S. PATENT DOCUMENTS

| 4,955,728 A | * | 9/1990 | Hebrank | ................ | A01K 43/00 |
| | | | | | 209/510 |
| 5,173,737 A | * | 12/1992 | Mitchell | ................ | A01K 45/00 |
| | | | | | 356/53 |

(Continued)

FOREIGN PATENT DOCUMENTS

| EP | 0675678 A | 10/1995 |
| WO | WO 2015/145435 A1 | 10/2015 |
| WO | WO 2017/204636 A2 | 11/2017 |

OTHER PUBLICATIONS

PCT Search Report with Written Opinion, International Application No. PCT/US2018/016578, International Filing Date Feb. 2, 2018, dated May 11, 2018.
(Continued)

*Primary Examiner* — David J Parsley
(74) *Attorney, Agent, or Firm* — Scott C. Mayhew (57) ABSTRACT

A pathogen reduction tool implementing a method of processing eggs at a poultry hatchery is provided. Such a method includes setting a production quantity of avian eggs in a setter incubator, the eggs being maintained in a plurality of egg flats. The avian eggs are removed from the setter incubator on a predetermined day of incubation, such predetermined day being during about day nine to day twelve of incubation. Subsequent to removal of the avian eggs from the setter incubator, the avian eggs are subjected to an egg detection system on the predetermined day to determine which of the avian eggs are viable and non-viable. The non-viable avian eggs are removed from the egg flats on the predetermined day. The viable avian eggs remaining in the egg flats post-inspection by the egg detection system are incubated through hatch.

6 Claims, 4 Drawing Sheets

(51) Int. Cl.
*A01K 45/00* (2006.01)
*A01K 41/06* (2006.01)

(58) Field of Classification Search
USPC ............................................. 119/6.8; 356/53
See application file for complete search history.

(56) References Cited

U.S. PATENT DOCUMENTS

| | | | | |
|---|---|---|---|---|
| 5,575,237 | A * | 11/1996 | Ferguson | A01K 41/00 119/300 |
| 5,745,228 | A * | 4/1998 | Hebrank | G01N 33/085 356/53 |
| 6,234,320 | B1 * | 5/2001 | Hebrank | A01K 43/00 209/510 |
| 7,289,196 | B2 | 10/2007 | Reeves et al. | |
| 7,861,673 | B2 * | 1/2011 | Huisinga | A01K 41/00 119/300 |
| 9,435,732 | B2 * | 9/2016 | Rozenboim | G01N 21/31 |
| 2013/0319335 | A1 * | 12/2013 | Hebrank | G01N 33/085 119/6.8 |
| 2015/0136988 | A1 † | 5/2015 | Walukas | |

OTHER PUBLICATIONS

Adjanohoun, Importance of automated candling and egg removal during incubation, pp. 7-9, Oct. 2016, International Hatchery Practice, vol. 30 (9).†

Ernst et al., Egg Candling and Breakout Analysis, pp. 1-9, 2004, ANR Publication 8134.†

Roto et al., Applications of In Ovo Technique for the Optimal Development of the Gastrointestinal Tract and the Potential Influence of the Establishment of Its Microbiome in Poultry, pp. 1-13, Aug. 2016, Front. Vet. Sci. 3(63).†

Maudlin, Quality Control Procedures for the hatchery, pp. 1-24, Jan. 1993, Poultry Sciences 93-0001.†

Tullett, Investigating Hatchery Practice, pp. 1-48, Oct. 2009, Ross Tech.†

Zoetis, EMBREX VMD ERH Egg Removal Heartbeat Operator Manual, pp. 1-105, 2013.†

\* cited by examiner
† cited by third party

|  | FARM | # EGGS | TOTAL CHICKS HATCH | % Fertile | # Fertile | % Hatch Fertility | % Hatch Set | NO. OF ROTS | ROTS PER 1000,000 |
|---|---|---|---|---|---|---|---|---|---|
| Control Trial #1 | A | 2883 | 2216 | 82.9% | 2390 | 92.7% | 76.9% | 4 | 1.387 |
|  | B | 7788 | 5222 | 72.8% | 5673 | 92.1% | 67.1% | 1 | 0.128 |
|  | C | 1606 | 1025 | 70.0% | 1124 | 91.2% | 63.8% | 8 | 4.981 |
|  | D | 3908 | 2986 | 82.3% | 3218 | 92.8% | 76.4% | 0 | 0.000 |
|  | E | 764 | 569 | 78.9% | 603 | 94.4% | 74.5% | 1 | 1.309 |
|  | F | 4651 | 3624 | 86.4% | 4019 | 90.2% | 77.9% | 26 | 5.590 |
|  | G | 113 | 79 | 77.0% | 87 | 90.8% | 69.9% | 11 | 97.345 |
|  | H | 5230 | 3806 | 81.0% | 4235 | 89.9% | 72.8% | 31 | 5.927 |
| Control Trial #2 | I | 336 | 208 | 78.9% | 265 | 78.5% | 61.9% | 10 | 29.762 |
|  | J | 1176 | 936 | 86.6% | 1018 | 91.9% | 79.6% | 7 | 5.952 |
|  | K | 543 | 435 | 89.3% | 485 | 89.7% | 80.1% | 4 | 7.366 |
|  | L | 3176 | 2436 | 82.1% | 2608 | 93.4% | 76.7% | 29 | 9.131 |
|  | M | 1008 | 759 | 81.6% | 823 | 92.2% | 75.3% | 2 | 1.984 |
|  | N | 3864 | 2646 | 78.3% | 3025 | 87.5% | 68.5% | 31 | 8.023 |
|  | O | 241 | 141 | 79.3% | 191 | 73.8% | 58.5% | 3 | 12.448 |
|  | P | 1055 | 807 | 84.1% | 887 | 91.0% | 76.5% | 10 | 9.479 |
|  | Q | 698 | 526 | 84.4% | 589 | 89.3% | 75.4% | 12 | 17.192 |
|  | R | 1917 | 1243 | 77.2% | 1480 | 84.0% | 64.8% | 63 | 32.864 |
| Control Trial #3 | S | 216 | 144 | 77.3% | 167 | 86.2% | 66.7% | 12 | 55.556 |
|  | T | 1272 | 858 | 75.7% | 963 | 89.1% | 67.5% | 16 | 12.579 |
|  | U | 249 | 186 | 82.3% | 205 | 90.7% | 74.7% | 5 | 20.080 |
|  | V | 5342 | 3956 | 81.4% | 4351 | 90.9% | 74.1% | 75 | 14.040 |
|  | W | 222 | 171 | 84.7% | 188 | 91.0% | 77.0% | 32 | 144.144 |
|  | X | 1616 | 1256 | 85.6% | 1384 | 90.8% | 77.7% | 10 | 6.188 |
| TOTAL |  | 49874 | 36235 | 80.2% | 39978 | 90.6% | 72.7% | 403 | 8.080 |

FIG. 4

|  | FARM | # EGGS | TOTAL CHICKS HATCH | % Fertile | # Fertile | % Hatch Fertility | % Hatch Set | NO. OF ROTS | ROTS PER 1000.000 |
|---|---|---|---|---|---|---|---|---|---|
| Treatment Trial #1 | A | 2983 | 2231 | 78.6% | 2345 | 95.1% | 74.8% | 1 | 0.335 |
|  | B | 7920 | 5438 | 72.2% | 5720 | 95.1% | 68.7% | 0 | 0.000 |
|  | C | 1530 | 996 | 71.4% | 1092 | 91.2% | 65.1% | 1 | 0.654 |
|  | D | 3888 | 3016 | 80.1% | 3115 | 96.8% | 77.6% | 0 | 0.000 |
|  | E | 720 | 545 | 77.2% | 556 | 98.0% | 75.7% | 0 | 0.000 |
|  | F | 4627 | 3667 | 84.1% | 3891 | 94.2% | 79.3% | 3 | 0.648 |
|  | G | 102 | 75 | 107.8% | 110 | 68.2% | 73.5% | 0 | 0.000 |
|  | H | 5267 | 3922 | 79.2% | 4169 | 94.1% | 74.5% | 1 | 0.190 |
|  | I | 373 | 271 | 85.3% | 318 | 85.2% | 72.7% | 0 | 0.000 |
| Treatment Trial #2 | J | 1201 | 949 | 87.2% | 1047 | 90.6% | 79.0% | 0 | 0.000 |
|  | K | 543 | 439 | 89.1% | 484 | 90.7% | 80.8% | 0 | 0.000 |
|  | L | 3060 | 2353 | 80.3% | 2456 | 95.8% | 76.9% | 1 | 0.327 |
|  | M | 1008 | 729 | 78.1% | 787 | 92.6% | 72.3% | 4 | 3.968 |
|  | N | 3881 | 2657 | 73.4% | 2848 | 93.3% | 68.5% | 10 | 2.577 |
|  | O | 144 | 87 | 72.9% | 105 | 82.9% | 60.4% | 1 | 6.944 |
|  | P | 1056 | 793 | 79.7% | 842 | 94.2% | 75.1% | 3 | 2.841 |
|  | Q | 682 | 498 | 77.1% | 526 | 94.7% | 73.0% | 1 | 1.466 |
| Treatment Trial #3 | R | 1923 | 1330 | 74.5% | 1432 | 92.9% | 69.2% | 0 | 0.000 |
|  | S | 214 | 160 | 80.4% | 172 | 93.0% | 74.8% | 1 | 4.673 |
|  | T | 1296 | 893 | 73.6% | 954 | 93.6% | 68.9% | 4 | 3.086 |
|  | U | 250 | 155 | 76.0% | 190 | 81.6% | 62.0% | 5 | 20.000 |
|  | V | 5357 | 3901 | 77.5% | 4152 | 94.0% | 72.8% | 6 | 1.120 |
|  | W | 216 | 162 | 77.3% | 167 | 97.0% | 75.0% | 0 | 0.000 |
|  | X | 1617 | 1255 | 82.4% | 1333 | 94.1% | 77.6% | 3 | 1.855 |
| TOTAL |  | 49858 | 36522 | 77.8% | 38811 | 94.1% | 73.3% | 45 | 0.903 |

FIG. 5

METHOD FOR REDUCING PATHOGENS IN POULTRY HATCHERY OPERATIONS

CROSS REFERENCE TO RELATED APPLICATION

This application claims the benefit of U.S. Provisional Patent Application No. 62/455,761, filed Feb. 7, 2017, which is expressly incorporated herein by reference in its entirety.

TECHNICAL FIELD

The present disclosure generally relates to egg processing in poultry hatcheries. More particularly, the present disclosure relates to a method for reducing the incidence of pathogens present in avian egg hatchery operations.

BACKGROUND

The responsible use of antibiotics is one of many important tools in the treatment of animal disease. Poultry producers, however, are continuously seeking alternative ways to control disease while reducing antibiotic use, in response to consumer concerns about the use of antibiotics to treat and prevent disease in poultry. In poultry hatcheries, where eggs are incubated over the course of twenty-one days until the chicks hatch, pathogens may be found in eggs that are either infertile or non-viable (dead embryos). Such infertile or non-viable eggs may serve as incubators for pathogens to grow over the course of the twenty-one days of incubation.

Accordingly, it would be desirable to provide a method for reducing the incidence of pathogens present in poultry hatchery operations in order to reduce the need for antibiotic use.

BRIEF SUMMARY

The above and other needs are met by aspects of the present disclosure which, according to one aspect, provides a pathogen reduction tool implementing a method of processing eggs at a poultry hatchery. The method includes setting a production quantity of avian eggs in a setter incubator, the eggs being maintained in a plurality of egg flats. The avian eggs are removed from the setter incubator on a predetermined day of incubation, such predetermined day being during about day nine to day twelve of incubation. Subsequent to removal of the avian eggs from the setter incubator, the avian eggs are subjected to an egg detection system on the predetermined day to determine which of the avian eggs are viable and non-viable. The non-viable avian eggs are removed from the egg flats on the predetermined day. The viable avian eggs remaining in the egg flats post-inspection by the egg detection system are incubated through hatch.

Thus, various aspects of the present disclosure provide advantages, as otherwise detailed herein.

BRIEF DESCRIPTION OF THE DRAWINGS

Having thus described various embodiments of the present disclosure in general terms, reference will now be made to the accompanying drawings, which are not necessarily drawn to scale, and wherein:

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

Figure 1:
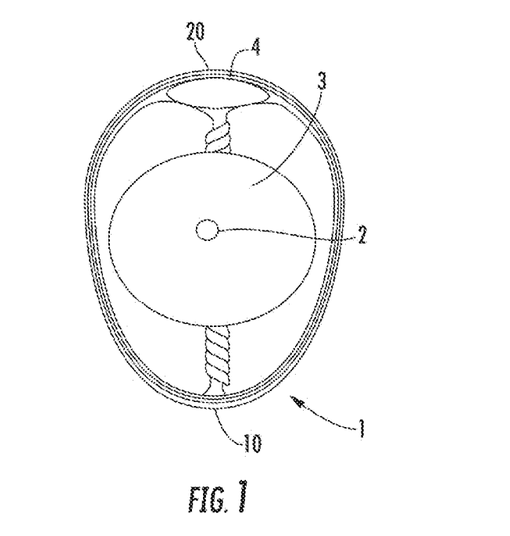
FIG. 1 illustrates a live chicken egg at about day one of incubation.
Figure 2:
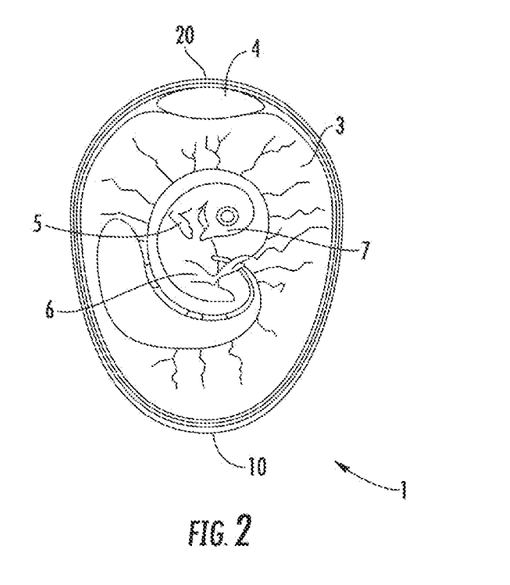
FIG. 2 illustrates a live chicken egg at about day eleven of incubation.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent the broadened end 20. As illustrated in FIG. 2, the wings 5, legs 6, and beak 7 of a baby chick have developed.

Eggs that do not hatch include eggs that were not fertilized, as well as fertilized eggs that have died. An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-viable" or "non-live" eggs because they do not include a living embryo.

In poultry hatchery operations, eggs are incubated for twenty-one days until hatch. The eggs are first placed in setter incubators and positioned in egg flats that maintain the eggs vertical along their longitudinal axis and allow air to circulate about the egg. At transfer day (Day 18 of incubation), the eggs are transferred into a hatching basket and placed into a hatcher incubator. The hatching basket is configured to allow the chicks to hatch and then move around. Taking advantage of this transfer where the eggs are removed from the incubators, hatchery operators candle the eggs on transfer day so as to facilitate removal of non-live eggs from the egg flats prior to transfer into the hatching baskets. Egg candling refers to the process of distinguishing live eggs from non-live eggs using various technologies, as known by those of skill in the art. Unfortunately, not all non-live eggs are removed at transfer day since such removal is dependent upon the accuracy of the candling technology employed by the hatchery, particularly with respect to mid-dead, late-dead and rotted eggs. Moreover, by transfer day, some of the infertile, early dead, mid-dead or late-dead eggs may have become rotted eggs capable of exploding and contaminating eggs proximate thereto.

It has been discovered and disclosed herein that removal of non-live eggs earlier in the incubation period, compared to current hatchery industry practice, significantly reduces the presence of pathogens and the risk of bio-contamination of the viable eggs. That is, by removing the non-viable eggs early in the incubation process, the non-viable eggs do not have adequate time to grow as much pathogenic material (when compared to current industry practice) that can contaminate otherwise viable eggs positioned adjacent or proximate to such non-viable eggs during a complete incubation period (Day 21 of incubation) or partial incubation period (Day 18 of incubation). In other words, removal of the non-viable eggs early in the incubation process reduces the potential pathogenic load that may be otherwise present throughout the incubation period, thereby increasing the yield of viable eggs and increasing hatch percentage. Moreover, by removing the non-viable eggs earlier in the incubation process, there is a resultant reduction in risk of horizontal transmission of pathogens during handling and incubation from Day 9-Day 21 of incubation. For example, mechanical handling of eggs at Day 18 of incubation typically causes the rotted eggs to explode and spread contaminants to other nearby or adjacent eggs (horizontal transmission). The disclosed methodology helps reduce this risk of horizontal transmission. There are other means of horizontal transmission of pathogens during Day 9-Day 21 of incubation, and the methodology disclosed herein is intended to reduce such risk associated therewith.

As previously described, poultry hatcheries candle eggs on day eighteen of incubation when the eggs are removed from the setter incubator, transferred from the egg flat carriers to hatching baskets, and placed into hatcher incubators. However, by day eighteen of incubation the rotted eggs have likely contaminated otherwise viable eggs. As mentioned previously, in some instances, early dead or mid-dead eggs may become rotted eggs that serve as breeding ground for pathogens. In this regard, by removing eggs earlier in the incubation process in accordance with the present disclosure, an operator may remove such early dead and mid-dead eggs before they become rotted eggs capable of contaminating otherwise viable eggs.

There exists interacting factors that support removal of all non-viable eggs from incubation between Day 9-12 as a unique pathogen reduction tool. One factor is physiological and is associated with the safe handling of live eggs during incubation. The other factor is microbiological and is associated with the nutrients within the egg and potential accessibility by possible pathogens.

Physiologically, safely handling an egg during incubation occurs between Day 9 and 12 of incubation. There are two primary reasons: one involves the need for turning the egg and the other is the need for heating or cooling the egg. The egg becomes exothermic between about Day 12 and 13 of incubation, generating between about 0.1774 and 0.2559 BTU of heat. Cooling the egg is needed after Day 13 of incubation and thus removal of heat is an important function in incubation after that time. Slowing development of the embryo may occur if lower than optimal heat is given, regardless of timing, but excessive heat will eradicate the embryo, also regardless of timing. High heat in the incubating environment is more probable after Day 13 of incubation due to the embryo generating its own heat.

There also exists an important point in incubation between about Day 1 and Day 8 where rotation of the egg is consistently provided (90 degree on vertical axis every hour) to simulate that of nature. A chicken normally turns an egg by rolling it in the nest up to 100 or more times per day. Commercial incubators may turn the egg once an hour (24 times per day). Physical need for turning perishes after about Day 7 to Day 8 of incubation, thus further supporting the safe handling of the egg in commercial incubation at Day 9 or later.

As previously described, non-viable eggs consist of infertile eggs as well as any eggs that contain embryos that die after incubation begins. These two types of eggs (infertile, early-dead) represent possible nutrient sources for bacteria and fungus. The nutrient is not albumen; it is the yolk material. The yolk is captured in the vitelline membrane and suspended in the albumen, as shown in FIG. 1. The yolk typically is not available for most bacterial and fungal access until after about 9 days of incubation. As albumen breaks down and liquefies (water is liberated) due to time and incubation temperature, the yolk (fatty acid) "floats" up in the albumen and comes into contact with the inner shell membranes.

Bacteria and fungus, trapped in the inner/outer shell membrane matrix (from laying/cooling process), may then potentially access the yolk nutrient and contaminate the egg. Earlier contamination of these non-viable eggs may occur in incubation, but is caused by cracked or imperfect shells. Typically these cracked eggs may be culled and not included in production.

Importantly, as provided in the present disclosure, removal of the non-viable infertile and early dead embryos at Day 9-12 removes the potential for bacterial and fungal growth at a safe time for development of the remaining live egg group, thus providing pathogen reduction by eliminating causative agents before contamination occurs.

Figure 3:
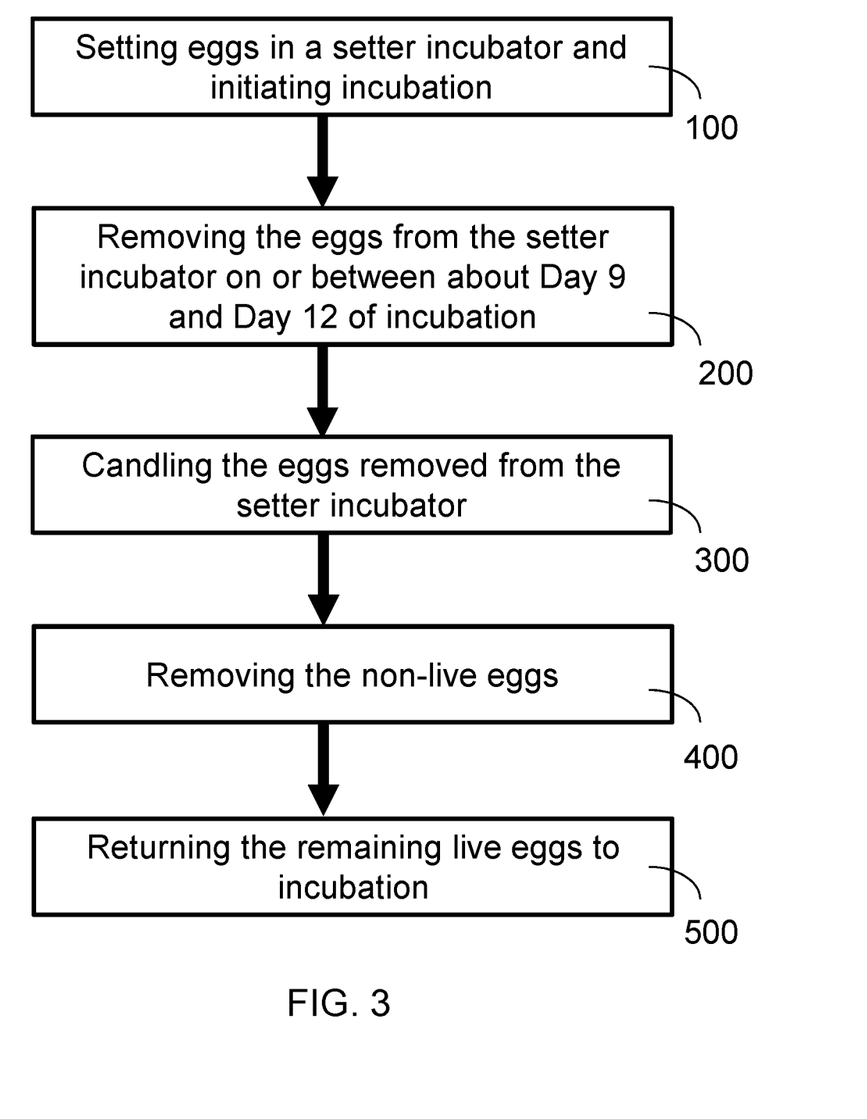
FIG. 3 is a flowchart illustrating a novel process capable of being used as a pathogen reduction tool in a commercial poultry hatchery, according to one aspect of the present disclosure.

The method of the present disclosure will now be described with reference to the figures. With initial reference to FIG. 3, illustrated is an exemplary method for processing avian eggs in order to reduce the incidence of pathogen exposure within a poultry hatchery operation. In this regard, the process disclosed herein may be provided as a pathogen reduction tool for commercial poultry hatchery operations.

Initially, a commercial production quantity of eggs may be delivered to the hatchery for hatching. The eggs may arrive in an egg flat or other similar container being configured based on the type of incubator equipment used by the hatchery. The egg flat may be specifically designed to expose as much of the egg as possible to air within the incubator, with the goal of achieving a uniform temperature environment about the egg. The incubation process may begin in a setter incubator (step 100) which has racks disposed therein that mate with the egg flats to facilitate movement of the eggs, thereby simulating the hen's movement of an egg in the nest. The first day of incubation is referred to as Day 1.

According to aspects of the present disclosure, the eggs may be removed from the setter incubator on about Day 9, Day 10, Day 11, or Day 12 of incubation (step 200). The data shown in FIG. 5 relate to eggs removed during Day 10 of incubation, but the present disclosure is not limited to such since it may be the case in which the days of incubation are calculated differently by individual hatcheries. That is, it will be understood that Day 10 as defined by Applicant as ten days from the start of incubation could be slightly different than that as defined by a hatchery that counts Day 0 as the first day of incubation such that Day 9 would be the equivalent of Applicant's Day 10. Accordingly, Applicant has provided the range of Day 9-12 of incubation as being in accordance with the present disclosure to account for such varied definitions. Moreover, it is expected that the process defined herein would be successful in reducing pathogenic load when implemented at any of Days 9-12 of incubation.

The eggs may be candled once removed from the setter incubator (step 300) to distinguish the live eggs from the non-live eggs. That is, the eggs may be subjected to an egg candling system (generally referred to herein as an egg detection system) capable of discriminating among the eggs to determine the viability of the eggs. Various candling systems may be used in the disclosed process, including those implementing technology related to spectroscopy, egg opacity, heartbeat/pulse identification, or other such known system. Advantageously, the process disclosed herein may improve the accuracy of some candling systems, particularly egg opacity candling systems that determine live versus non-live based on the amount of infrared light transmitted through the egg. Such egg opacity candling systems may utilize infrared pulses of light to identify non-viable eggs (most effectively, infertile and early-dead embryos) that have died during incubation. Typically, at Day 18 of incubation it may be difficult for egg opacity candling systems to distinguish mid-dead, late-dead or rotted eggs from a live egg since the embryo is almost at full size at Day 18 of incubation and therefore blocking most of the light from passing through the egg for detection. Thus, by moving the candling process earlier in the incubation period it may improve detection of rotted and/or mid-dead eggs so that these eggs can be removed to limit their potential negative impact or contamination on surrounding live eggs. Regardless of the candling system used, removing the non-live eggs during Days 9-12 of incubation reduces the opportunity for the infertile, early-dead, and mid-dead eggs to turn into rotted eggs that can explode when mechanically processed (injected, transferred to hatching baskets, removed, etc.) downstream.

Once the non-live eggs have been determined via candling at Days 9-12 of incubation, the non-live eggs may be removed from the egg flats (step 400) by an egg remover device, which may employ vacuum or mechanical means for lifting the non-live eggs from the egg flats in an automated manner. In some instances, the candling and removal functions may be performed by a single system (e.g., Embrex Egg Remover system, Embrex® ERH system, both available from Zoetis Inc.) in which the candling device communicates with the removal device for identifying and removing non-live eggs. In some instances, the candling system may employ technology for determining whether a heartbeat/pulse exists for a respective egg, or detecting movement of the embryo. Such a heartbeat/pulse signal or embryo movement signal may provide a positive indication that an embryo within the egg is alive. That is, such technology may rely upon determining whether there exists at least one of a periodic and aperiodic variation in an intensity of electromagnetic radiation transmitted through a respective egg corresponding to action of a heart or embryo movement, the existence of one of the periodic and aperiodic variations indicating that the avian egg is viable. This technology may rely upon the eggs being maintained within a certain temperature range such as, for example, between about 93° F. (34° C.) and 97° F. (36° C.) during the candling inspection process. As such, the eggs may be quickly moved to the candling system and passed therethrough, while monitoring of the egg temperatures is ongoing.

After removing the non-live eggs, the remaining live eggs may be returned for incubation. In some instances, the live eggs may remain in the egg flats and be returned to the setter incubators. At Day 18 of incubation, the eggs may be removed from the setter incubators and candled again to remove any remaining non-live eggs, particularly the late-dead eggs (embryos that died after the Day 9-12 candling procedure). The live eggs may be injected in some instances with a treatment substance such as a vaccine via an in ovo injection device (Embrex® Inovoject® system, available from Zoetis Inc.). Regardless of whether the eggs are candled again or injected, the live eggs may be transferred to hatching baskets using an egg transfer table device (Embrex® Transfer Table system, available from Zoetis Inc.). After placement into the hatching baskets, the live eggs are moved into a hatcher incubator where the eggs will hatch at about Day 21 of incubation.

In other instances, however, the live eggs may be transferred to hatching baskets via the egg transfer table device during Day 9-12 of incubation, rather than at the typical Day 18 of incubation. Such a transfer may be desirable during Day 9-12 of incubation if no further processing (e.g., candling, injection) of the eggs is desired prior to hatch, which may be acceptable due to the reduction in pathogenic load facilitated by the process disclosed herein.

Implementation of the disclosed methods herein have been shown to provide a greater than 100× reduction in visible rots at Day 18, and also a reduction in early mortality from about 6-8% to about 1%. With improved candling technology, it is expected that the reduction in possible rots may be achievable to about 1,000%.

A further understanding of the disclosure may be obtained from the non-limiting example that follows below.

EXAMPLE

In each trial, eggs were received from various farms of the hatchery and randomly split into two groups for segregated incubation and hatching. The control group eggs were incubated in a standard "Jamesway 84" (JW84) incubation tray (egg flat holding 84 eggs). The control group was removed from the setter incubator on Day 18 of incubation. An Embrex® Egg Remover system was used to candle the eggs and then remove the non-live eggs from the JW84 incubation tray. The eggs remaining in the JW84 incubation tray were transferred to hatching baskets via automation during Day 18 of incubation. The hatching baskets were moved into hatcher incubators until hatch.

The treatment group eggs were incubated in a standard "Jamesway 36" (JW36) incubation tray (egg flat holding 36 eggs). An Embrex® ERH system was configured to utilize a JW36 incubation tray. The treatment group eggs were removed from the setter incubator during Day 10 of incubation and candled utilizing the ERH system. The ERH system processed two JW36 incubation trays at one time using 72 individual candling detection devices. All non-viable eggs were removed with selective vacuum cups. The live eggs remained in the JW36 incubation tray and were placed back into the setter incubator. Egg shell temperature was monitored during the ERH candling process and maintained between 97° F. and 93° F. Eggs were removed from the setter incubators for approximately 20-35 minutes. On Day 18 of incubation, the treatment group eggs were transferred by hand into hatching baskets. The treatment group eggs were hatched in separate hatcher incubators from the control group eggs.

For both groups, microbial monitoring was conducted and included environmental air plates and swabs of egg shell surfaces and hatched chicks (liver/yolk). Quantitative measurements were made with regards to visibly or obviously contaminated eggs removed during transfer (Day 18) as well as standard categorical analysis of unhatched eggs (necropsy) after hatch (Day 21).

Figure 4:
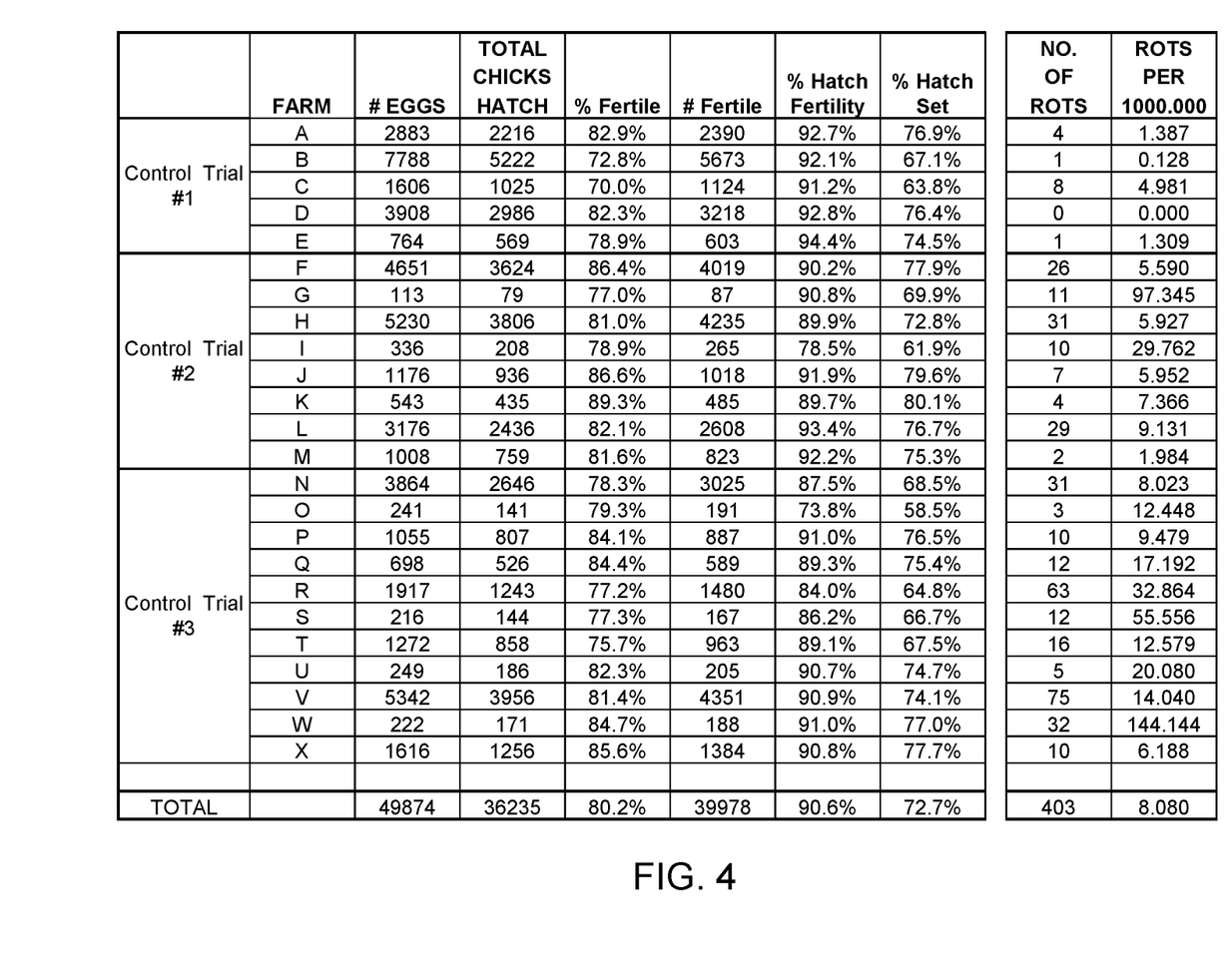
FIG. 4 is a table of data for a control group of eggs generated for comparison to a treatment group in various trials.
Figure 5:
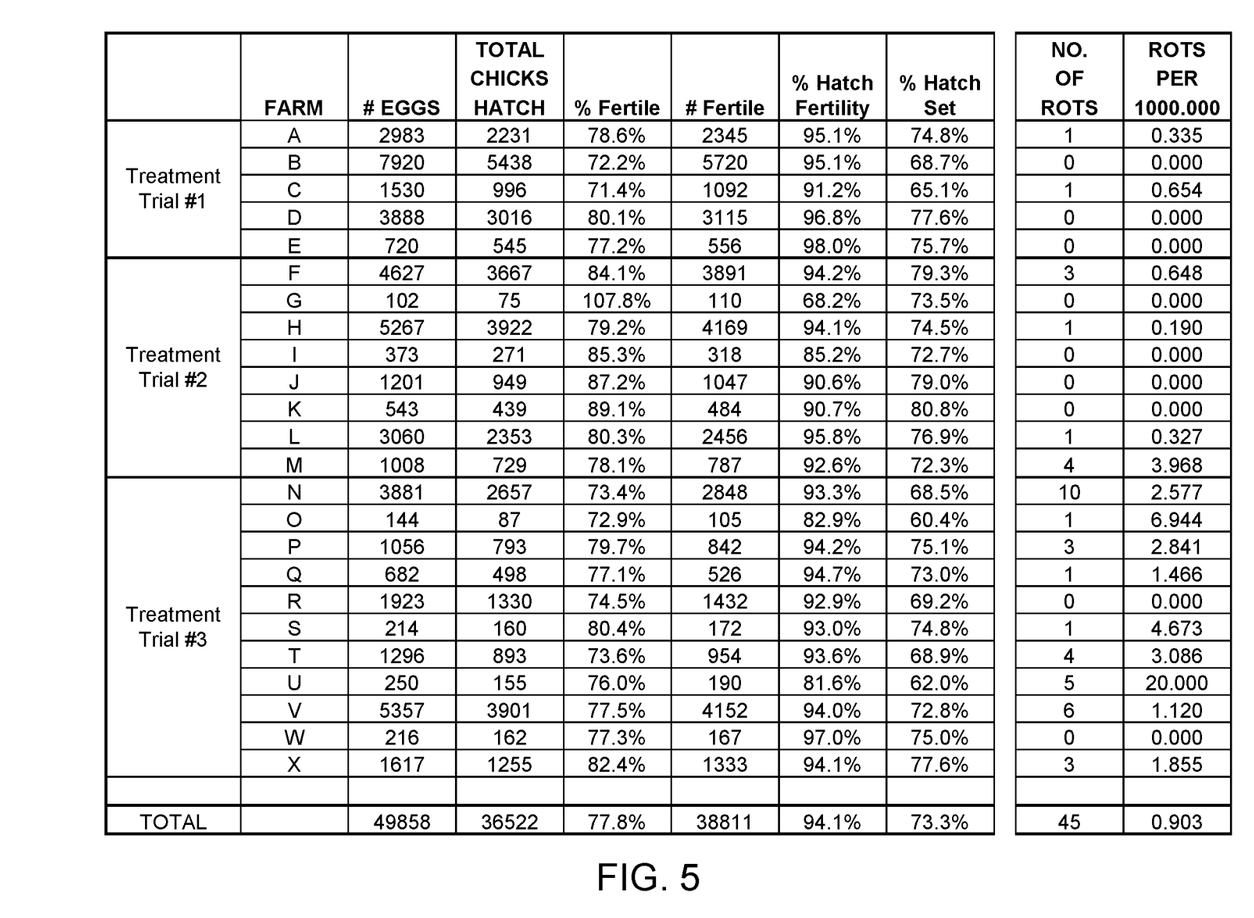
FIG. 5 is a table of data for a treatment group of eggs subjected to a process implemented as a pathogen reduction tool in a commercial hatchery, for comparison against the data of FIG. 4.

FIG. 4 is a table of data generated with respect to the control group eggs for Trials 1-3. FIG. 5 is a table of data generated with respect to the treatment group eggs for Trials 1-3. Control Trial #1 and Treatment Trial #1 were conducted on the same date. Control Trial #2 and Treatment Trial #2 were conducted on the same date, but on a different date from Trial #1. Control Trial #3 and Treatment Trial #3 were conducted on the same date, but on a different date from Trial #1 and Trial #2. Improvements can be seen in production measurements of percentage hatch ("% Hatch Set") and hatch of fertile eggs ("% Hatch Fertility") due to treatment. The hatch of fertile eggs is based on the number of eggs determined to be live by the respective egg candling system. There is also a significant reduction in visible or obviously rotted eggs present during Day 18 transfer ("Rots per 1000.000" eggs set). The number of rots shown in FIGS. 4 and 5 was determined during transfer (Day 18).

TABLE 1

Egg Necropsy Summary - results of unhatched egg analysis

| Trial # | Group | Rot/Egg Set | Rot % | Late Dead/ Egg Set | Late Dead % |
|---|---|---|---|---|---|
| 1 | Control | 20/1680 | 1.19 | 17/1680 | 1.01 |
|  | Treatment | 0/1440 | 0 | 12/1440 | 0.83 |
| 2 | Control | 10/2520 | 0.40 | 46/2520 | 1.83 |
|  | Treatment | 0/2160 | 0 | 25/2160 | 1.16 |
| 3 | Control | 23/3024 | 0.76 | 33/3024 | 1.09 |
|  | Treatment | 1/2592 | 0.04 | 19/2592 | 0.73 |
| Total | Control | 53/7224 | 0.733 | 96/7224 | 1.329 |
|  | Treatment | 1/6192 | 0.016 | 56/6192 | 0.904 |

Table 1 shows a large reduction of rotten eggs and reduced late mortality (late-dead) found during necropsy of unhatched eggs. The data provided in Table 1 is the result of necropsy analysis of unhatched eggs for the respective Control and Treatment groups. In this regard, the number of rots in Table 1 represents rotten eggs that were not removed during transfer (Day 18) due to candling limitations (either manual or automated), but were discovered during necropsy. Thus, the number of rots in Table 1 represents additional reduction in rots due to treatment as those tabulated in FIG. 5. That is, Table shows the level of rots undetected at Day 18 transfer (visible) and represents an additional difference due to treatment.

TABLE 2

Candling Accuracy Summary

| Trial # | Group | Infertile and Early Dead | Infertile/ Early Dead % | Mid-Dead | Mid-Dead % |
|---|---|---|---|---|---|
| 1 | Control | 3/1680 | 0.18 | 14/1680 | 0.83 |
|  | Treatment | 3/1440 | 0.21 | 14/1440 | 0.97 |

TABLE 2-continued

Candling Accuracy Summary

| Trial # | Group | Infertile and Early Dead | Infertile/ Early Dead % | Mid-Dead | Mid-Dead % |
|---|---|---|---|---|---|
| 2 | Control | 41/2520 | 1.63 | 18/2520 | 0.71 |
|  | Treatment | 3/2160 | 0.14 | 6/2160 | 0.28 |
| 3 | Control | 81/3024 | 2.68 | 37/3024 | 1.22 |
|  | Treatment | 4/2592 | 0.15 | 13/2592 | 0.50 |
| Total | Control | 125/7224 | 1.730 | 69/7224 | 0.955 |
|  | Treatment | 10/6192 | 0.161 | 33/6192 | 0.533 |

Table 2 shows a summary of early-dead/infertile eggs and mid-dead eggs found during necropsy of unhatched eggs. This data shows the relative efficiency of the egg candling systems used to remove the non-viable eggs.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method of reducing pathogenic load at a poultry hatchery, the method comprising:
   setting a production quantity of avian eggs in a setter incubator, the eggs being maintained in a plurality of egg flats;
   removing the avian eggs from the setter incubator on a predetermined day of incubation, such predetermined day being during about day nine to day twelve of incubation;
   subsequent to removing the avian eggs from the setter incubator, subjecting the avian eggs to an egg detection system on the predetermined day to determine which of the avian eggs are viable and non-viable;
   removing the non-viable avian eggs from the egg flats on the predetermined day to reduce an available pathogenic load among the avian eggs; and
   incubating through hatch the viable avian eggs remaining in the egg flats post-inspection by the egg detection system, whereby the yield of viable eggs and hatch percentage are increased due to removal of the non-viable eggs on the predetermined day.

2. A method according to claim 1, further comprising the steps of removing the viable avian eggs from incubation on about day eighteen of incubation and injecting a treatment substance into the viable avian eggs.

3. A method according to claim 2, further comprising the steps of transferring the injected avian eggs to a plurality of hatching baskets and placing the egg-filled hatching baskets within a hatcher incubator.

4. A method according to claim 1, further comprising the step of transferring the viable avian eggs to a plurality of hatching baskets on the predetermined day, and wherein incubating through hatch the viable avian eggs remaining in the egg flat comprises placing the egg-filled hatching baskets within a hatcher incubator.

5. A method according to claim 1, further comprising the step of maintaining the avian eggs at a temperature of between about 93° F. (34° C.) and 97° F. (36° C.) after removal from the setter incubator on the predetermined day.

6. A method according to claim 1, wherein subjecting the avian eggs to an egg detection system comprises determining whether there exists at least one of a periodic and aperiodic variation in an intensity of electromagnetic radiation transmitted through a respective avian egg corresponding to action of a heart or embryo movement, the existence of one of the periodic and aperiodic variations indicating that the avian egg is viable.

* * * * *